(12) United States Patent
Cohen

(10) Patent No.: US 11,801,379 B2
(45) Date of Patent: Oct. 31, 2023

(54) AORTIC CONNECTORS AND METHODS OF USE

(71) Applicant: TC1 LLC, St. Paul, MN (US)

(72) Inventor: Sarah Cohen, Cambridge, MA (US)

(73) Assignee: TC1 LLC, St. Paul, MN (US)

( * ) Notice: Subject to any disclaimer, the term of this patent is extended or adjusted under 35 U.S.C. 154(b) by 127 days.

(21) Appl. No.: 17/244,573

(22) Filed: Apr. 29, 2021

(65) Prior Publication Data

US 2021/0244938 A1 Aug. 12, 2021

Related U.S. Application Data

(62) Division of application No. 15/957,504, filed on Apr. 19, 2018, now Pat. No. 11,020,583.

(Continued)

(51) Int. Cl.
*A61M 60/863* (2021.01)
*A61M 60/411* (2021.01)
(Continued)

(52) U.S. Cl.
CPC ........ *A61M 60/863* (2021.01); *A61M 60/178* (2021.01); *A61M 60/183* (2021.01); *A61M 60/196* (2021.01); *A61M 60/232* (2021.01); *A61M 60/237* (2021.01); *A61M 60/411* (2021.01); *A61M 60/419* (2021.01);
(Continued)

(58) Field of Classification Search
CPC .............. A61M 60/863; A61M 60/178; A61M 60/183; A61M 60/196; A61M 60/232; A61M 60/237; A61M 60/411; A61M 60/419; A61M 60/822; A61M 60/824; A61M 60/825; A61M 60/859;
(Continued)

(56) References Cited

U.S. PATENT DOCUMENTS 4,712,551 A 12/1987 Rayhanabad
5,695,471 A 12/1997 Wampler
(Continued)

FOREIGN PATENT DOCUMENTS

WO 2005067577 7/2005
WO 2007038109 4/2007
(Continued)

*Primary Examiner* — Amanda K Hulbert
*Assistant Examiner* — Natasha Patel
(74) *Attorney, Agent, or Firm* — Kilpatrick Townsend & Stockton LLP

(57) ABSTRACT

Connectors and related methods for fluidly coupling a blood pump with an aorta facilitate implantation of the blood pump. A method of fluidly coupling a blood pump with an aorta includes positioning a connector device defining a passageway extending between a proximal opening and a distal opening. The connector device includes a support member surrounding the distal opening. The support member is interfaced with a wall of the aorta so that the distal opening is at a desired location of an inlet opening in the aorta. The support member is attached to the aorta around the distal opening so as to form a fluid seal and stabilize the connector device. A slit is incised in the wall of the aorta to form the inlet opening in the aorta. A proximal opening of the tubular connector is fluidly coupled with an outflow graft tube of the blood pump.

18 Claims, 14 Drawing Sheets

Related U.S. Application Data

(60) Provisional application No. 62/488,596, filed on Apr. 21, 2017.

(51) Int. Cl.

| | | |
|---|---|---|
| *A61M 60/825* | (2021.01) | |
| *A61M 60/183* | (2021.01) | |
| *A61M 60/237* | (2021.01) | |
| *A61M 60/232* | (2021.01) | |
| *A61M 60/88* | (2021.01) | |
| *A61M 60/822* | (2021.01) | |
| *A61M 60/824* | (2021.01) | |
| *A61M 60/859* | (2021.01) | |
| *A61M 60/196* | (2021.01) | |
| *A61M 60/178* | (2021.01) | |
| *A61M 60/419* | (2021.01) | |
| *A61B 17/11* | (2006.01) | |
| *A61M 60/148* | (2021.01) | |

(52) U.S. Cl.
CPC ........ *A61M 60/822* (2021.01); *A61M 60/824* (2021.01); *A61M 60/825* (2021.01); *A61M 60/859* (2021.01); *A61M 60/88* (2021.01); *A61B 17/11* (2013.01); *A61B 2017/1107* (2013.01); *A61M 60/148* (2021.01); *A61M 2205/8206* (2013.01)

(58) Field of Classification Search
CPC ................ A61M 60/88; A61M 60/148; A61M 2205/8206; A61B 17/11; A61B 2017/1107
See application file for complete search history.

(56) References Cited

U.S. PATENT DOCUMENTS

| | | | |
|---|---|---|---|
| 6,071,093 A | 6/2000 | Hart | |
| 6,116,862 A | 9/2000 | Rau et al. | |
| 6,186,665 B1 | 2/2001 | Maher et al. | |
| 6,234,772 B1 | 5/2001 | Wampler et al. | |
| 6,264,635 B1 | 7/2001 | Wampler et al. | |
| 6,471,633 B1 | 10/2002 | Freed | |
| 6,688,861 B2 | 2/2004 | Wampler | |
| 7,699,586 B2 | 4/2010 | LaRose et al. | |
| 7,976,271 B2 | 7/2011 | LaRose et al. | |
| 7,997,854 B2 | 8/2011 | LaRose et al. | |
| 8,007,254 B2 | 8/2011 | LaRose et al. | |
| 8,152,493 B2 | 4/2012 | LaRose et al. | |
| 8,562,508 B2 | 10/2013 | Dague et al. | |
| 8,652,024 B1 | 2/2014 | Yanai et al. | |
| 8,668,473 B2 | 3/2014 | LaRose et al. | |
| 11,020,583 B2 | 6/2021 | Cohen | |
| 2003/0023255 A1* | 1/2003 | Miles ................ | A61M 60/865 606/158 |
| 2003/0078592 A1* | 4/2003 | Heilman ............ | A61M 60/859 606/108 |
| 2004/0002624 A1* | 1/2004 | Yu ...................... | A61M 60/857 600/16 |
| 2006/0111733 A1 | 5/2006 | Shriver | |
| 2007/0078293 A1 | 4/2007 | Shambaugh et al. | |
| 2007/0213690 A1 | 9/2007 | Phillips et al. | |
| 2008/0021394 A1 | 1/2008 | Larose et al. | |
| 2009/0203957 A1 | 8/2009 | Larose et al. | |
| 2012/0046514 A1 | 2/2012 | Bourque | |
| 2012/0095281 A1 | 4/2012 | Reichenbach et al. | |
| 2013/0096364 A1 | 4/2013 | Reichenbach et al. | |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0225909 A1 | 8/2013 | Dormanen et al. | |

FOREIGN PATENT DOCUMENTS

| | | |
|---|---|---|
| WO | 2011043888 | 4/2011 |
| WO | 2011109747 | 9/2011 |
| WO | 2013023009 | 2/2013 |

* cited by examiner

Section C-C

AORTIC CONNECTORS AND METHODS OF USE

CROSS-REFERENCE TO RELATED APPLICATIONS

The present application is a Divisional of U.S. patent application Ser. No. 15/957,504 filed Apr. 19, 2018 (Allowed); which claims the benefit of U.S. Provisional Appln No. 62/488,596 filed Apr. 21, 2017, the disclosures which are incorporated herein by reference in their entirety for all purposes.

BACKGROUND

This application relates generally to connectors that interface with a patient's natural vasculature, in particular, connectors that interface a mechanical circulatory support system implanted in a patient with the aorta of the patient.

Ventricular assist devices, known as VADs, are implantable blood pumps used for both short-term (i.e., hours, days, months) and long-term applications (i.e., years or a lifetime) where a patient's heart is incapable of providing adequate circulation, for example, due to heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function.

While blood pumps have been effective for many patients, because patients using such devices are living longer, further improvements that prolong the effectiveness and lifetime of such blood pump devices are desired. One challenge is that inconsistencies in implantation can adversely affect performance of the blood pump. Another challenge is that changes in blood flow where the blood pump interfaces with the patient's natural vasculature can lead to formation of thrombus. Thus, there is a need for improved connectors that interface mechanical circulatory support systems with a patient's natural vasculature and for methods of implantation that provide consistency and predictability and avoid thrombus formation over the lifetime of the device.

BRIEF SUMMARY

In one aspect, an anastomosis connector device is provided for fluidly coupling a blood pump to an aorta of a patient. In some embodiments, the connector device includes a tubular connector configured for providing a path for blood flow therethrough. The tubular connector defines a blood flow passageway extending from an inlet opening adapted for coupling with an outflow graft tube of the blood pump to a distal opening configured for delivering blood flow into the aorta at a desired angle. In some embodiments, the tubular connector is attached to a support member adapted to attach to a surface of a body vessel. In some embodiments, the tubular connector is surrounded by a substantially planar portion (e.g., flange or flexible graft material) adapted for attachment to a surface of the aorta to stabilize the connector device and associated blood flow path when the connector is attached to the outflow graft of the pump. The planar portion is substantially planar relative to the tubular connector. In some embodiments, the tubular connector extends at a set angle relative the substantially planar portion, or the tubular connector is defined with a blood flow path of a set diameter; the connector can be selected according to a desired angle or a desired diameter as needed for a particular application or patient morphology. In various embodiments, the support member or planar portion is substantially rigid relative to the vessel wall or associated graft. In one aspect, the support member or planar portion is defined so as to provide a more stable base for attachment of the outflow graft tube as compared to conventional anastomosis techniques. Such an aortic connector provides a number of advantages over the conventional approach of attaching a graft tube described further below.

One advantage use of such an aortic connector provides is more consistent flow resistance in the aortic anastomosis region. The aortic connector provides a relatively rigid template to which the opening in the aorta is attached such that there is minimal or reduced variation in the diameter of the opening (no "necking down") and a consistent angle of entry from the outflow graft to the aorta. As smaller graft diameters and smaller, more efficient pumps, consistency in this region may allow pumps to be more finely tuned.

Another advantage use of such an aortic connector provides is optimal or improved washing in the aortic root. Various studies have investigated the best angle for the flow to enter the ascending aorta from the outflow graft. Insufficient washing of the aortic root area may risk flow stasis and subsequent thrombus. Surgeons currently approximate the cut angle of the outflow graft, but this connector may allow for a more precise and consistent angle for all patients. The inlet angle can be any angle within a range of 10 to 120 degrees, typically preferred at an angle within a range of about 45 degrees to about 60 degrees, often about 45 degrees. It is appreciated that the preferred angle can vary based on the application and anatomy of the patient.

Yet another advantage use that such an aortic connector can provide is improved ease of operation and implantation, particularly when the connector includes use of mechanical coupling features (e.g., quick connect couplings). In such embodiments, attachment of the graft end to the connector can be performed quickly and easily by a simple, turn/lock, snap/lock or push/lock type mechanism, as compared to performing manual suturing. In such embodiments, the first, more complex suturing step would only require a simple, small connector to be present in the surgical window. The outflow graft could then be attached via a quick coupling mechanism to the connector. As surgeons move to less invasive techniques and smaller incisions, breaking down the surgery into less cumbersome steps is beneficial.

Still another advantage use that an aortic connector provides is allowing for a full-length supported graft. Improved graft tubes are being developed that include physically integrating a stiffer polymer winding onto the outside of the graft material itself. This winding would then remove the need for a separate outflow graft bend relief component, since it would prevent the graft from kinking or crimping. One development hurdle is determining the end condition of the graft with this winding, given the conventional implantation procedure including cutting off a distal end of the graft tube at a desired length and angle and directly suturing the cut-off end of the graft tube to a slit opening in the aorta. Since cutting the end of the graft tube at an angle can be problematic if reinforcing winding or hoops are provided in this portion and further since any exposed reinforcement materials at the distal end risks damaging the soft aortic wall at the anastomosis, typically, the distal portion of the graft omits such reinforcing winding or hoops. Use of an aortic connector can allow the reinforcement material to extend all the way from the pump to the aorta so as to support the entire graft. In some embodiments, the graft's aortic end could be incorporated into the aortic connector, thereby protecting the aorta. In some embodiments, the actual reinforcing material can be used to couple the graft tube to the connector, for example, one of a series of reinforcement hoops along a length of the graft tube can be captured by a coupling feature of the aortic connector.

In various embodiments described herein, the connector device includes a substantially planar portion surrounding the tubular connector along or near the distal opening and a tubular connector extending from the planar portion and adapted for attachment to the outflow graft tube. The substantially planar portion is configured for placement against a wall of the aorta. In some embodiments, the planar portion is defined to extend along a curved plane, so as to accommodate the curved wall of an artery, such as the aorta. In some embodiments, the substantially planar portion is formed of a flexible material, such as a graft material, so as to conform to a contoured surface, such as an outer surface of the aorta. The connector device can further include one or more attachment features to facilitate secure attachment of the planar portion with the aorta as well as secure attachment of the connector to the outflow graft tube. In some embodiments, the tubular connector is configured to extend linearly from the planar portion at an angle. Typically, the angle is between 30 and 75 degrees from perpendicular, more typically, between 45 and 60 degrees from perpendicular. In some embodiments, multiple connector devices or tubular connector components are provided having a range of differing sizes, diameters or angles for selection by a physician as desired for a particular application and/or anatomy of the patient.

In some embodiments, the planar portion of the connector is formed of a flexible graft material so as to conform to an outside surface of the wall of the aorta. The flexible graft material can be of a porous or textured material so as to promote tissue in-growth with the wall of the aorta. In some embodiments, the planar portion is formed of a material to allow suturing of the planar portion to the wall of the aorta. The planar portion can include a suture ring circumscribing the distal opening to facilitate attachment of the connector device to the wall of the aorta by one or more sutures. In some embodiments, the flexible graft material is attached to the surface of the aorta and then the graft tube is attached directly to the graft material about an opening formed in the graft material for blood flow into the aorta, thereby providing a more consistent, stable interface for attachment of the graft tube as compared to directly suturing the graft tube to the aorta.

In some embodiments, the aortic connector device includes a planar portion defined as a flange for engaging an inside surface of the wall of the aorta and a tubular connector extending from the flange through the wall of the aorta. The flange can be defined of a material suitable for suturing with the wall of the aorta. In some embodiments, the flange material is porous or textured so as to promote tissue in-growth with the wall of the aorta. The flange can be of a rigid or semi-rigid construction so as to facilitate secure anchoring of the connector and provide sufficient support to maintain the tubular connector at an angle into the aorta.

In some embodiments, the tubular connector and the planar portion are defined as a single integral component. In other embodiments, the tubular connector and planar portion are separate components that are provided fixedly coupled together or are assembled and sealingly coupled by the physician during implantation. In some embodiments, the planar portion and the tubular connector include interfacing coupling features for sealing the tubular connector about the inlet opening of the planar portion. Such interfacing coupling features can include any of: a snap-fit coupling, an interference fit, twist-and-lock, a screw ring, a capture ring, and an interfacing cuff.

In some embodiments, the aortic connector includes a tubular connector having an outflow tube attachment feature along or near a proximal opening thereof that is configured to fluidly couple tubular connector to an outflow tube of the blood pump. The outflow tube attachment feature can include a pair of interfacing components to secure and fluidly couple the tubular connector to the outflow tube of the blood pump. The one or more attachment features can include any of a threaded connection, a capture ring, a cuff, a snap-fit connection, a barbed connection, a twist-and-lock type connection or any combination thereof. In some embodiments, the outflow tube attachment features comprises a capture coupling feature adapted to capture a reinforcing hoop of the outflow graft tube, the tube having been cut to a desired length and including a series of reinforcing hoops along at least a distal portion thereof. In some embodiments, the tubular connector extending from the planar portion can also be defined of a material to facilitate suturing of the outflow graft tube thereto and may further include a suture ring for such purposes.

In another aspect, methods of fluidly coupling an outflow graft tube of a blood pump to an aorta of a patient with an aortic connector are provided herein. In some embodiments, such methods include coupling the aortic connector so as to interface with an outer surface of the aorta, while in other embodiments, the methods include coupling the aortic connector so as to engage an inside surface of the aorta.

In some embodiments, the method includes clamping a side portion of the aorta to create a hemostatic seal; positioning a connector device having a tubular connector extending between a proximal opening and a distal opening and a planar portion surrounding the distal opening so that the substantially planar portion interfaces a wall of the aorta and the distal opening is at a desired entry opening in the aorta. A slit is incised in the wall of the aorta to form the desired opening in the aorta. The substantially planar portion is then securely attached to the wall of the aorta around the distal opening. Securely attaching the planar portion to the aorta can include suturing the planar portion along a suture ring extending around the distal opening of the connector device so as to form a fluid seal. An outflow graft of the blood pump is then fluidly coupled to a proximal portion of the tubular connector to facilitate blood flow from the blood pump into the aorta. The coupling between the outflow graft to the tubular connector can include use of one or more mechanical coupling features to facilitate ease and consistency of attachment. In some embodiments, the coupling between the graft tube and the tubular connector is without sutures. In some embodiments, the method includes fluidly coupling a separate tubular connector to the planar portion by use of one or more mechanical coupling features. In some embodiments, the method includes cutting the graft tube to a desired length, the graft tube having circumferential reinforcement rib or hoops along at least a distal portion thereof, and securely attaching the proximal portion of the tubular connector to the graft tube by capturing a reinforcement hoop of the graft tube with the mechanical interface feature of the tubular connector. Such methods can include selecting the connector device or the tubular connector from a plurality of connector devices or tubular connectors defined with differing pre-determined angles in accordance with a desired blood flow angle for a particular application or an anatomy of the patient.

For a fuller understanding of the nature and advantages of the present invention, reference should be made to the ensuing detailed description and accompanying drawings.

BRIEF DESCRIPTION OF THE DRAWINGS

Further details, aspects, and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
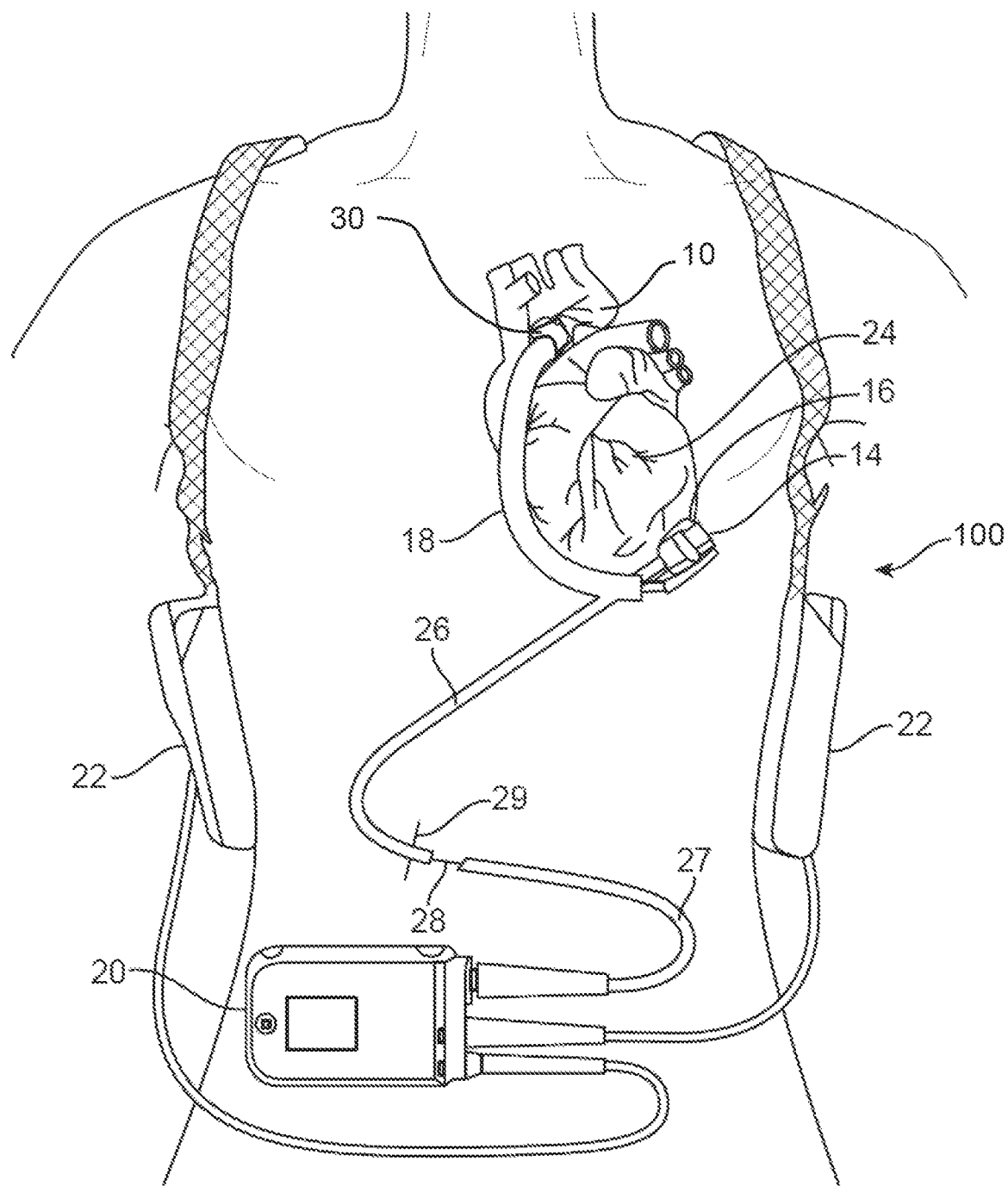
FIG. 1 is an illustration of a mechanical circulatory support system implanted in a patient's body with an aortic connector in accordance with some embodiments of the invention.

FIG. 1 illustrates a mechanical circulatory system TOO, including a VAD, that is used to partially or completely replace the function of a failing heart. Some VADs are intended for short term use, typically for patients recovering from heart attacks or heart surgery, while others are intended for long term use (e.g., years, and the remainder of a user's life), typically for patients suffering from congestive heart failure. VADs are designed to assist either the right (RVAD) or left (LVAD) ventricle, or both at once (BiVAD). VADs can be designed with an axial flow or centrifugal flow configuration. The impeller may be suspended by journal bearing such as a ball and cup, or by magnetic or hydrodynamic forces or both. In other embodiments, the blood pump can be an artificial heart, which is designed to completely take over cardiac function and may require the removal of a patient's heart. It should be appreciated that the technical features disclosed herein apply equally to any variation of the blood pump as described in this disclosure.

The VAD may comprise a centrifugal (as shown) or axial flow pump that is capable of pumping the entire output delivered to the left ventricle from the pulmonary circulation (i.e., up to 10 liters per minute). It is appreciated that the aortic connector can be used with various types of circulatory systems having differing types of blood pumps. Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,419,609, 8,652,024, 8,668,473, 8,852,072, 8,864,643, 8,882,744, 9,068,572, 9,091,271, 9,265,870, and 9,382,908, all of which are incorporated herein by reference for all purposes in their entirety.

The mechanical circulatory support system 100 of FIG. 1 includes an implantable blood pump 14, ventricular cuff 16, outflow cannula 18, system controller 20, and power sources 22. The implantable blood pump 14 is attached to an apex of the left ventricle, although it is appreciated that in some embodiments, a VAD can be attached to the right ventricle or both ventricles of the heart 24. The blood pump 14 may be attached to the heart 24 via the ventricular cuff 16 which is sewn to the heart 24 and coupled to the blood pump 14. The other end of the blood pump 14 connects to the ascending aorta via the outflow cannula 18 via an aortic connector 30 so that the VAD effectively diverts blood from the weakened ventricle and propels it to the aorta for circulation to the rest of the patient's vascular system. The mechanical circulatory support system 100 is depicted during battery 22 powered operation. The percutaneous cable 26 connects the implanted blood pump 14 to the system controller 20 through driveline cable 27. The percutaneous cable 26 exits the patient's abdomen at aperture 29 and connects to the driveline at modular connection 28. The system controller 20 monitors system operations and powered by an external power source 22. It will be appreciated that although the system controller 20 and power source 22 are illustrated outside/external to the patient body, the driveline cable 27, system controller 20 and/or power source 22 may be partially or fully implantable within the patient, as separate components or integrated with the blood pump 14. Examples of such modifications are further described in U.S. Pat. Nos. 8,562,508 and 9,079,043, all of which are incorporated herein by reference for all purposes in their entirety.

In conventional circulatory systems, surgeons must create a sutured connection between the aorta and the prosthetic graft of the outflow cannula exiting the blood pump. The connection at the aorta completes the blood flow loop which starts inside the left ventricle, travels through the pmp, exits through the outflow cannula through the prosthetic graft tube and flows into the aorta. To create the aortic anastomosis with the graft tube of the outflow cannula, a surgeon first clamps the side of the aorta and cuts a slit in the clamped aortic tissue. The surgeon then cuts the prosthetic graft to a desired length at a desired angle and uses a running suture to connect the open angled end of the graft tube around the slit in the aorta. Although this approach is widely used and accepted, variability in the graft end angle and suturing technique may cause differences in pressure drop across the interface and can also adversely affect blood flow washing in the aortic root. Problems with pressure drop across the interface may require modifying parameters of the pump in order to optimize performance, or in some cases, may require performing a revision of the aortic anastomosis. In order to improve performance and effectiveness of the blood pump over its lifetime, it is desirable to create a consistent interface between the prosthetic graft tube of the outflow cannula and the aorta, particularly in regard to the size of the opening and the angle at which the prosthetic tube enters the aorta.

In one aspect, the invention provides an aortic connector adapted for attachment to the prosthetic graft tube at a pre-determined opening size or angle. The aortic connector maintains hemostasis to the aorta and the graft. Such an aortic connector having a set opening size and angle would effectively eliminate variability in the aortic anastomosis and allow for improve consistency and predictability in blood pump performance. Such an aortic connector can also improve ease of implantation for the surgeon. The aortic connector can be attached to the aorta and the graft tube by suturing, by use of a mechanical method, or by a combination of suturing and mechanical attachment methods. In some embodiments, the aortic connector is configured for attachment to the graft tube by a suture-less, mechanical attachment method. Typically, the aortic connector is attached to the aorta by use of a running suture circumscribing the opening, although it is appreciated that various suture-less means of attachment can also be used.

In one aspect, the aortic connector includes a planar portion extending around an opening of a set size to allow passage of blood from the prosthetic graft tube. The planar portion can be configured so as to conform to an outside of the aorta, can be formed so as to be disposed along an inside of the aorta, or can be formed so as to engage a wall of the aorta between interfacing portions of the connector. In some embodiments, the aortic connector is configured to rest solely outside of the aorta, not including any sutures that may extend into the aorta. In other embodiments, the aortic connector can include a portion that remains inside the aorta. The aortic connector can be configured as a single integral component. Such an integral component can further include additional coupling components (e.g., capture rings, threaded components, etc.). In other embodiments, the aortic connector can be configured as two or more components that couple together, for example, a planar portion that mounts to the wall of the aorta and couples with a separable tubular connector so as to extend from the planar portion at a pre-determined angle desired for blood flow into the aorta.

Figure 2A:
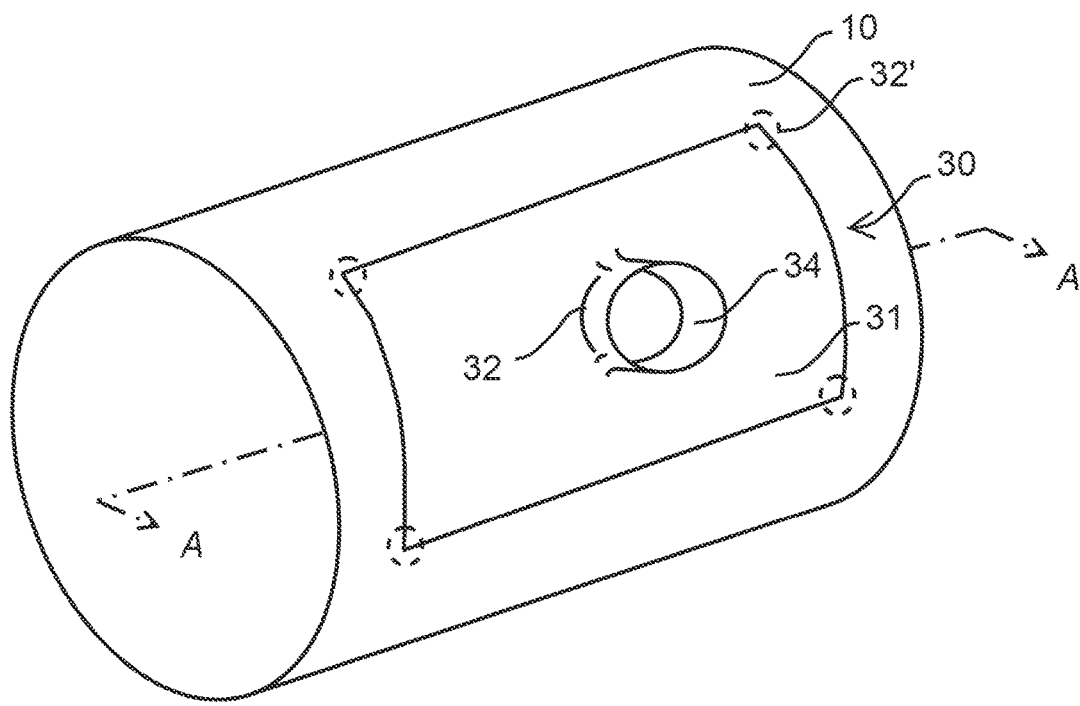
FIG. 2A and FIG. 2B show detail views of an aortic connector implanted on an aorta and subsequent connection of the aortic connector with an outflow graft tube from a blood pump, respectively, in accordance with some embodiments.
Figure 2B:
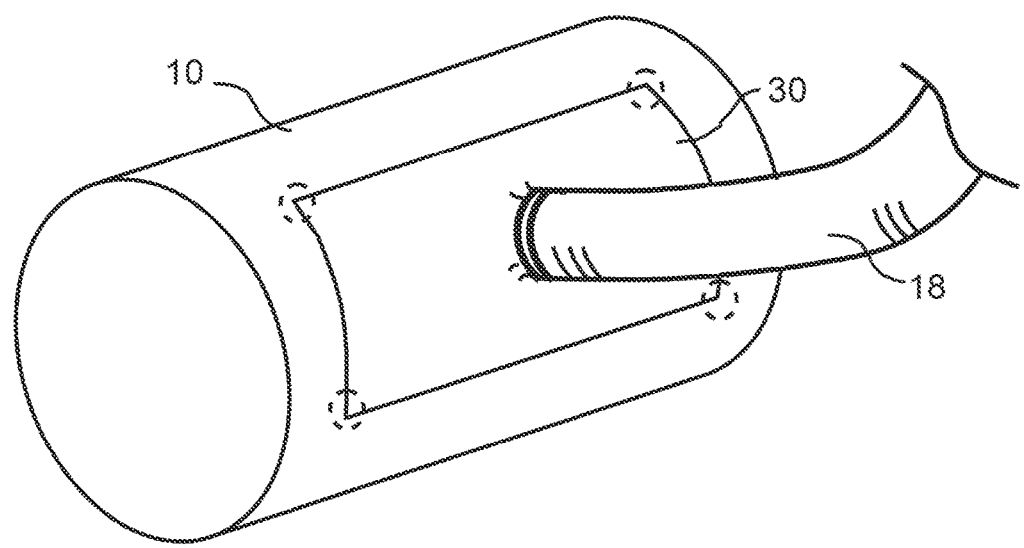

FIGS. 2A-2B illustrate an example aortic connector 30 adapted to be attached to an outside surface of the aorta. As shown in FIG. 2A, the aortic connector 30 includes a planar portion 31 that attaches to an outside wall of the aorta from which an angled tubular connector 34 extends. An outflow graft tube 18 is then coupled to the proximal opening of the tubular connector 34, as shown in FIG. 2B. Various aspects of this aortic connector 30 can be further understood by referring to the detail view of FIG. 3 and FIG. 4, which depicts a sectional view along section A-A in FIG. 2A.

Figure 3:
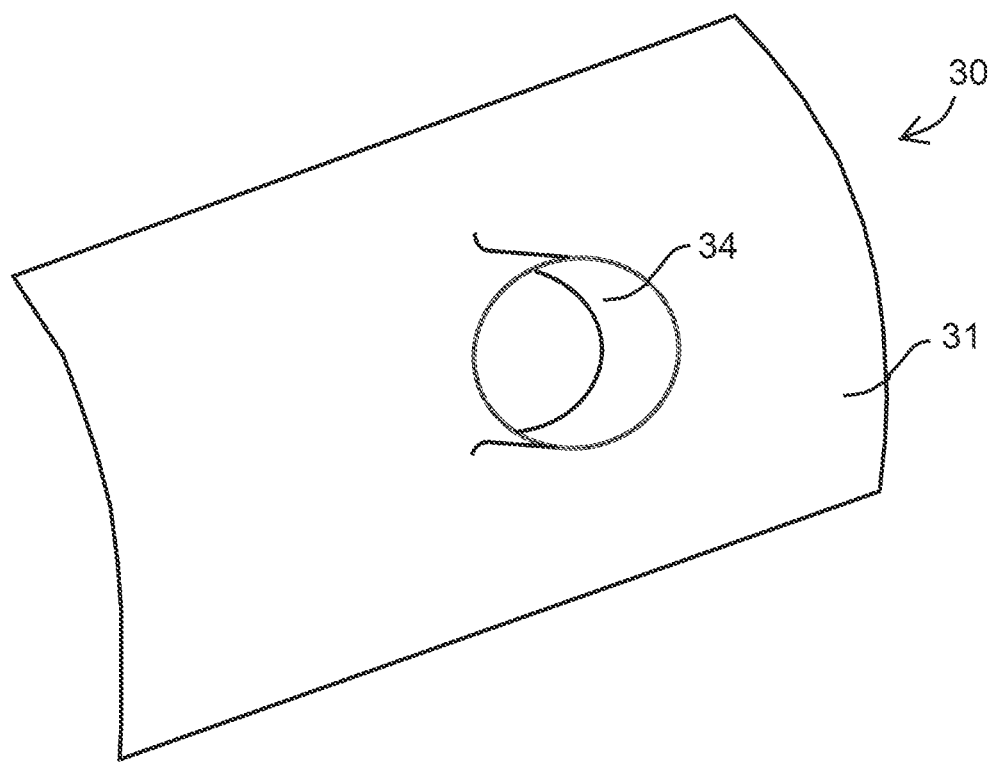
FIG. 3 shows an example aortic connector in accordance with some embodiments.
Figure 4:
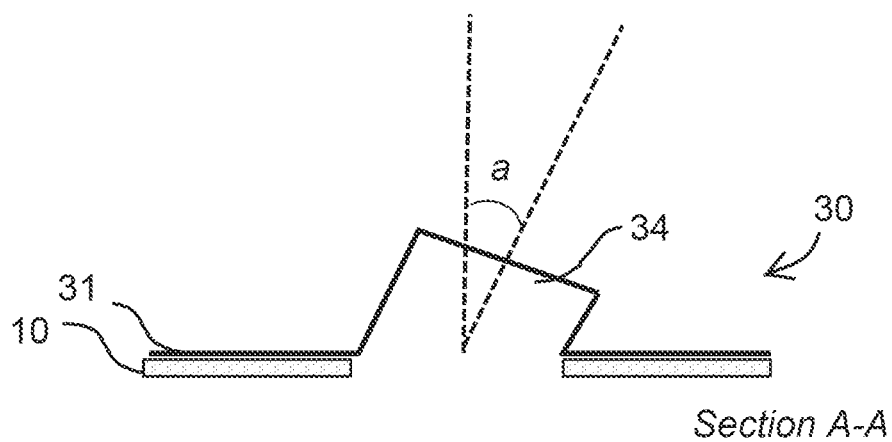
FIG. 4 shows a cross-sectional view of an implanted aortic connector in accordance with the embodiments of FIGS. 2A and 3.

As can be seen in FIG. 3, the aortic connector 30 includes a planar portion 31 that is formed of a flexible material so as to conform to an outer wall of the aorta. The flexible material can be a formed of a graft material or a membrane that is porous or textured so as to promote tissue in-growth. In some embodiments, the planar portion is semi-rigid and shaped to conform to an outside surface of the aorta. In this embodiment, the aortic connector 30 includes a suture ring 32 circumscribing the central opening of the connector. The suture ring 32 can be formed of a rigid or semi-rigid material (e.g., metal or hard plastic) and can be coupled to or integrated with the planar portion of the connector. Suturing the suture ring 32 to the wall of the aorta around a slit or opening in the aorta wall ensures the opening in the aorta is maintained at a set size and shape and maintains a hemostatic seal between the connector and the aorta. The outside corners or periphery of the flexible membrane can be tacked to the aorta by one or more sutures 32' or any suitable means (e.g., adhesive) so as to conform the flexible membrane to the outside surface of the aorta, as shown in FIG. 2A. Typically, the planar portion extends further beyond the suture ring, for example, anywhere from 1 to 10 cm, so as to facilitate anchoring of the connector with the aorta. The planar portion can also help maintain the protruding tubular connector 34 that interfaces with the graft tube at a pre-determined angle a, for example, an angle within a range of about 30-70 degrees from perpendicular, typically about 45 to 60 degrees. In this embodiment, the tubular connector 34 is permanently fixed with the planar portion 31. The tubular connector 34 can be formed of the same material as the planar portion, although typically of a thicker more rigid construction, or can be formed of a different material.

Figure 5:
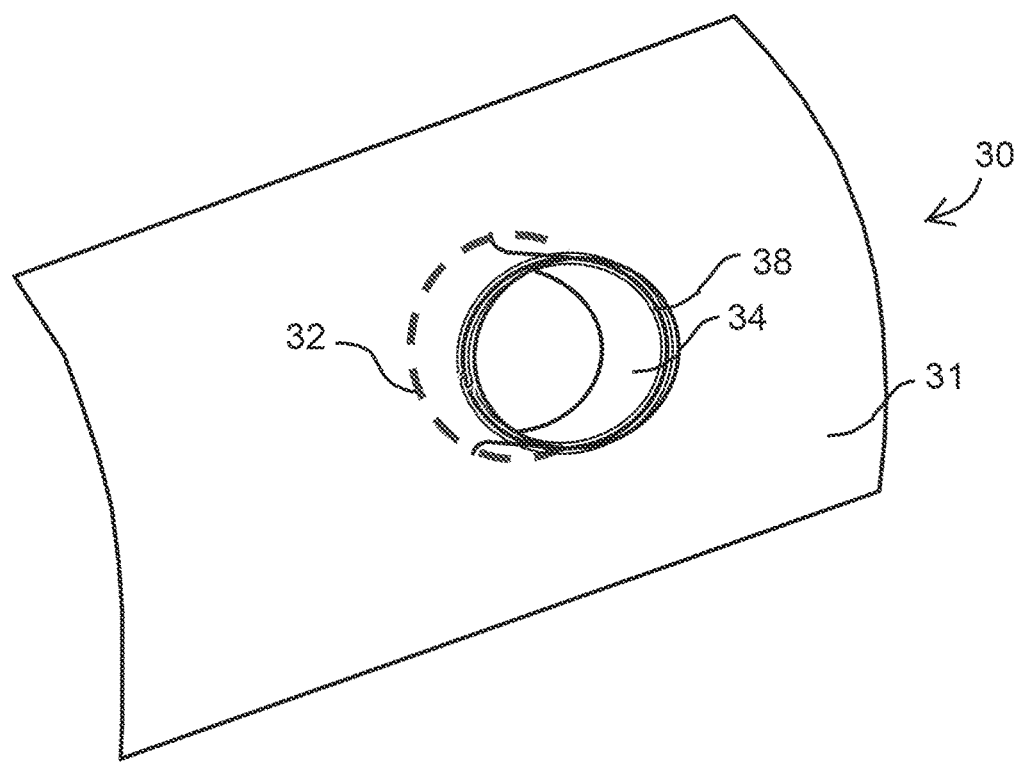
FIG. 5 shows another example aortic connector with an integrated suture ring and threaded graft tube attachment feature in accordance with some embodiments.
Figure 6:
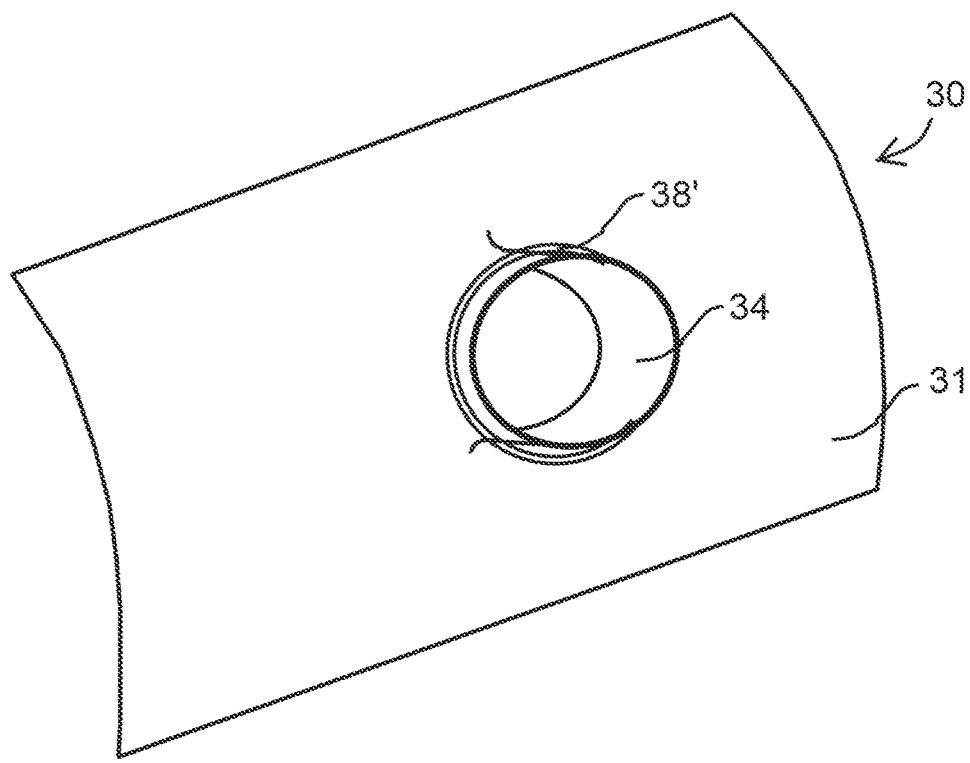
FIG. 6 shows another example aortic connector with a capture ring feature for attachment of a graft tube in accordance with some embodiments.

As shown, the protruding tubular connector 34 extends from an inlet opening to an outlet opening along the direction of blood flow therethrough, the planar portion 31 surrounding the tubular connector along or near the distal opening. A proximal portion of the tubular connector 34 is adapted to couple with the graft tube 18. In some embodiments, the tubular connector 34 is formed of a graft material that can be directly connected to the graft tube, such as by one or more sutures. The tubular connector 34 can include a suture ring around the proximal opening to facilitate direct suturing to the distal end of the graft tube 18. In other embodiments, the tubular connector includes an outflow attachment feature at or near the proximal opening to facilitate sealed attachment to the graft tube, such as shown in FIGS. 5-6. Such attachment features can further improve ease and consistency in how the graft tube and connector is attached, as compared to directly suturing the graft tube to an opening of the aorta.

FIG. 5 shows an example aortic connector having an integrated suture ring 32 and an outflow tube attachment feature 38 defined as a threaded portion along the proximal opening of the tubular connector 34. In this embodiment, the graft tube 18 can include a corresponding threaded ring along a distal portion thereon to facilitate secure sealing attachment between the graft tube 18 and tubular connector 34.

FIG. 6 shows another example aortic connector 30 that includes an outflow tube attachment feature 38' defined as a capture ring designed to capture a distal end of the graft tube 18 or a corresponding connector. In this embodiment, the graft tube 18 can include a distal ring or connector attached by one or more sutures, or any suitable means (e.g., heat sealing, adhesive) to facilitate capture of the distal ring along the proximal opening of the tubular connector 34 upon tightening of the capture ring.

Figure 7A:
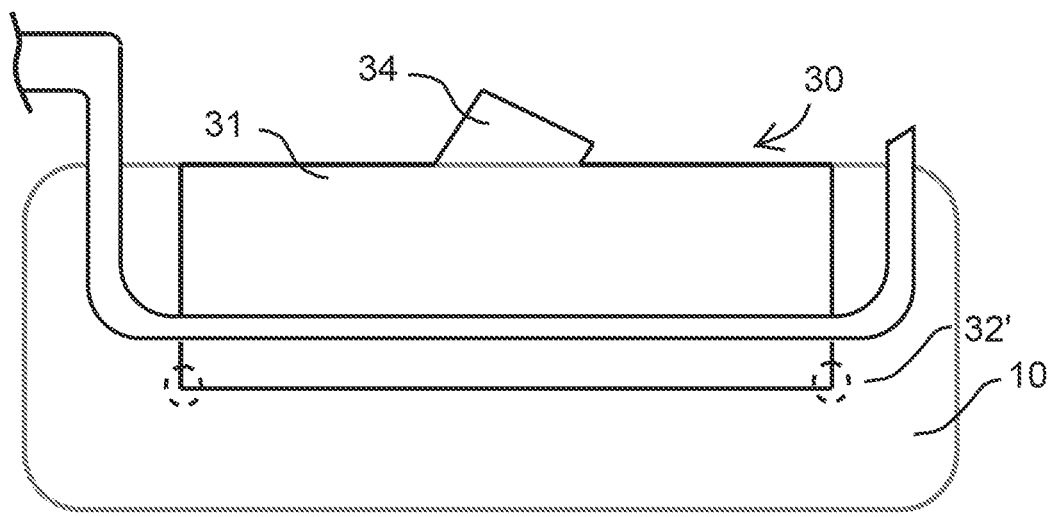
FIGS. 7A-7D show a method of attaching a graft tube of a blood pump to an aorta with an aortic connector in accordance with some embodiments.
Figure 7B:
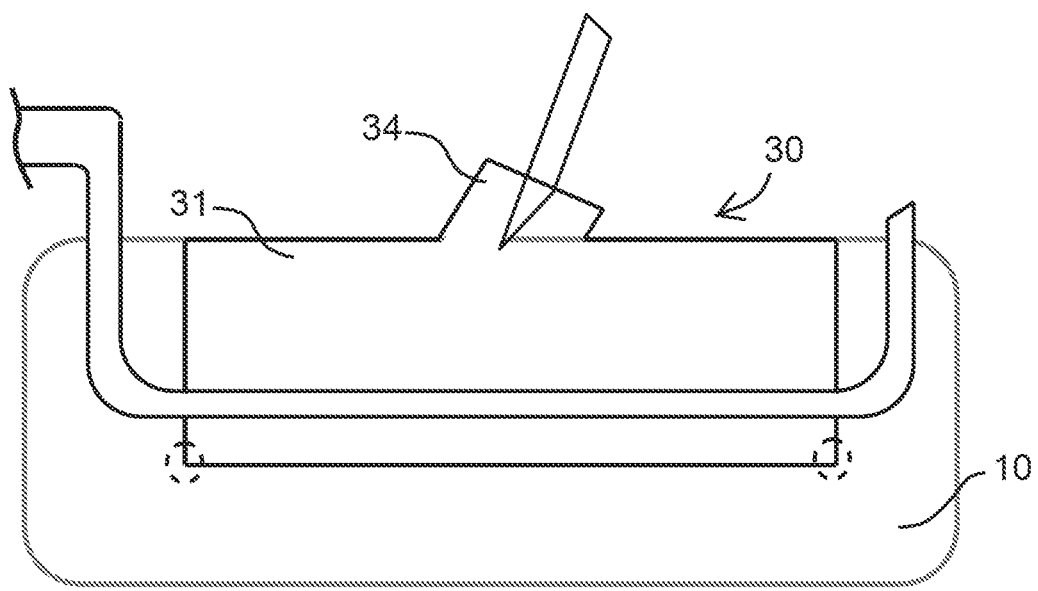
Figure 7C:
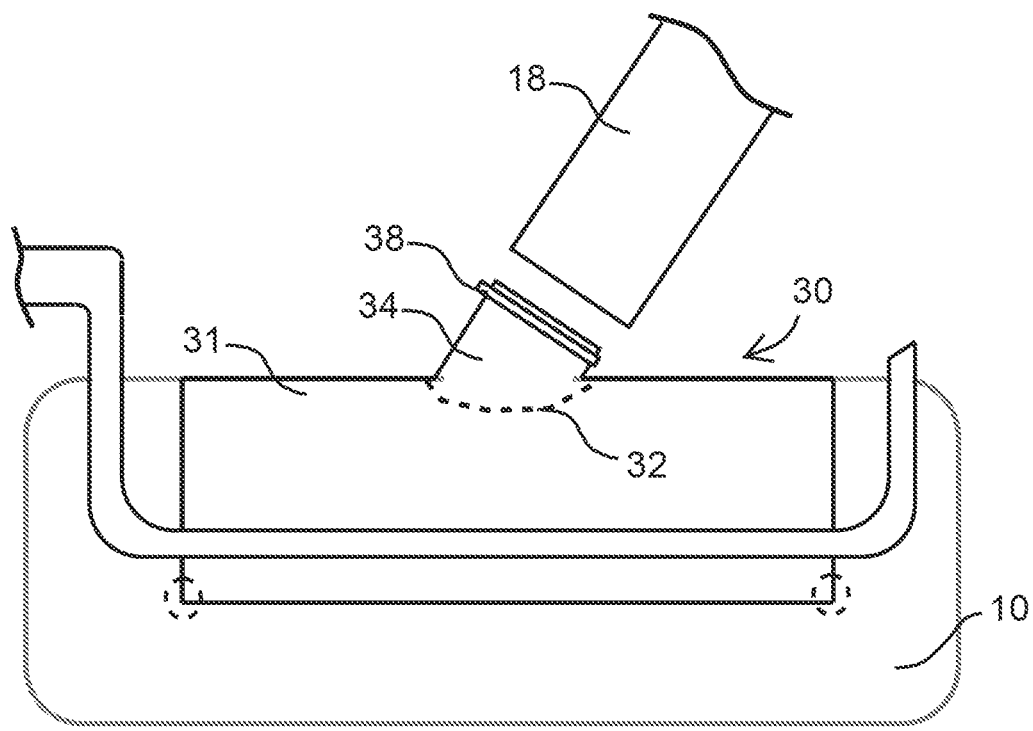
Figure 7D:
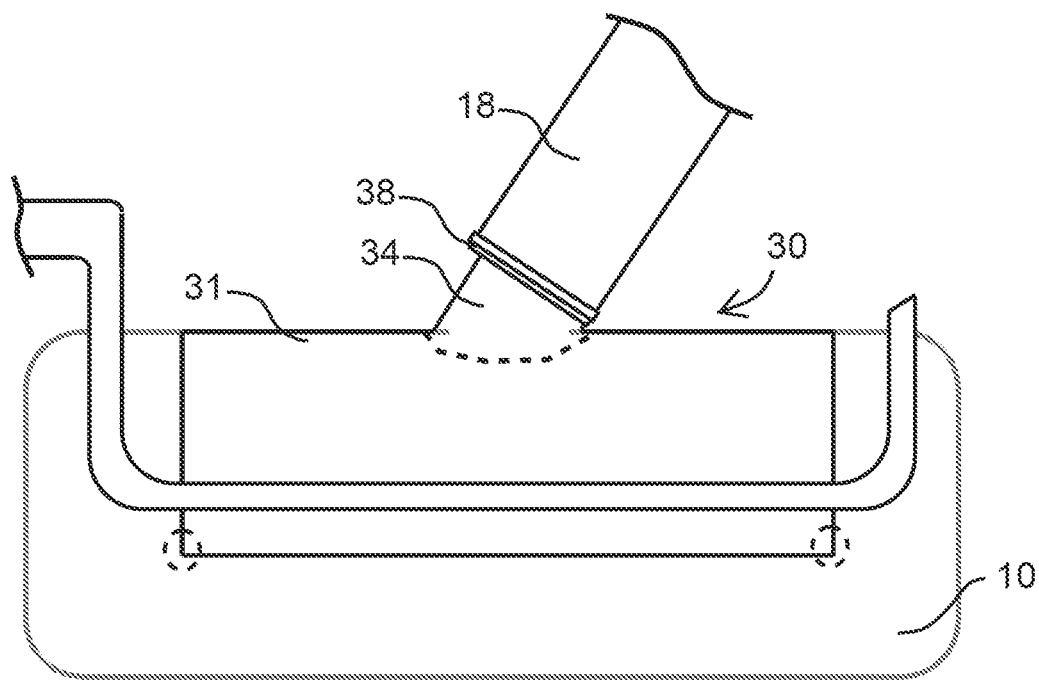

FIGS. 7A-7D depicts a method of attachment of an example aortic connector 30, such as that in FIG. 3, to an aorta and subsequent attachment of a graft tube to the connector, in accordance with some embodiments. As shown in FIG. 7A, the aortic connector 30 is attached to the outside surface of the aorta by applying the flexible material of the planar portion to the outer surface of the aorta so that the tubular connector 34 extends in a desired direction. Each corner of the flexible membrane is tacked to the surface by one or more sutures 32'. A side biting clamp is applied to the aorta to create a hemostatic seal, which seals the portion of the aorta to which the connector is being applied while still allowing blood flow through the remaining unclamped portion of the aorta. As shown in FIG. 7B, the portion of the aorta within the distal opening of tubular is slit open to form the desired inlet opening in the aorta for blood flow from the blood pump. As shown in FIG. 7C, the edges of the slit are then sutured directly to the inner diameter of the distal opening of the tubular connector. In this embodiment, the edges are sutured to a suture ring 32 circumscribing the opening of the connector 30. As shown in FIG. 7D, a graft tube 18 is then attached to the proximal opening of the tubular connector via an outflow tube attachment feature 38. The attachment feature 38 can be defined to utilize any of the coupling features described herein, or as any suitable means of attachment that would be known to one of skill in the art. Typically, the tubular connector 34 is angled such that the end of the graft tube 18 does not have to be cut at an angle and can be applied directly to the connector or through an intervening connector fitting. This approach provides improved consistency in the angle at which the outflow graft tube 18 extends to the aorta and also maintains the diameter of the blood flow path entering the aorta.

Figure 8:
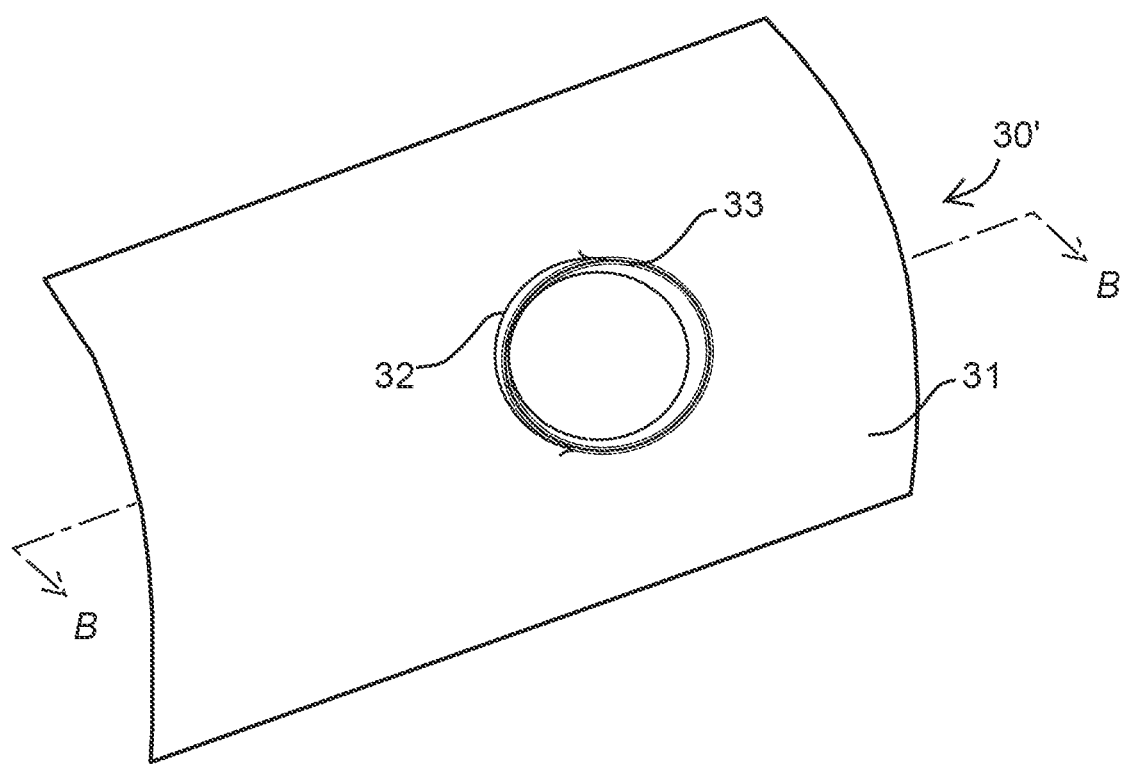
FIG. 8 shows another example aortic connector with a coupling feature for attaching a graft tube or an angled graft tube connector in accordance with some embodiments.
Figure 9:
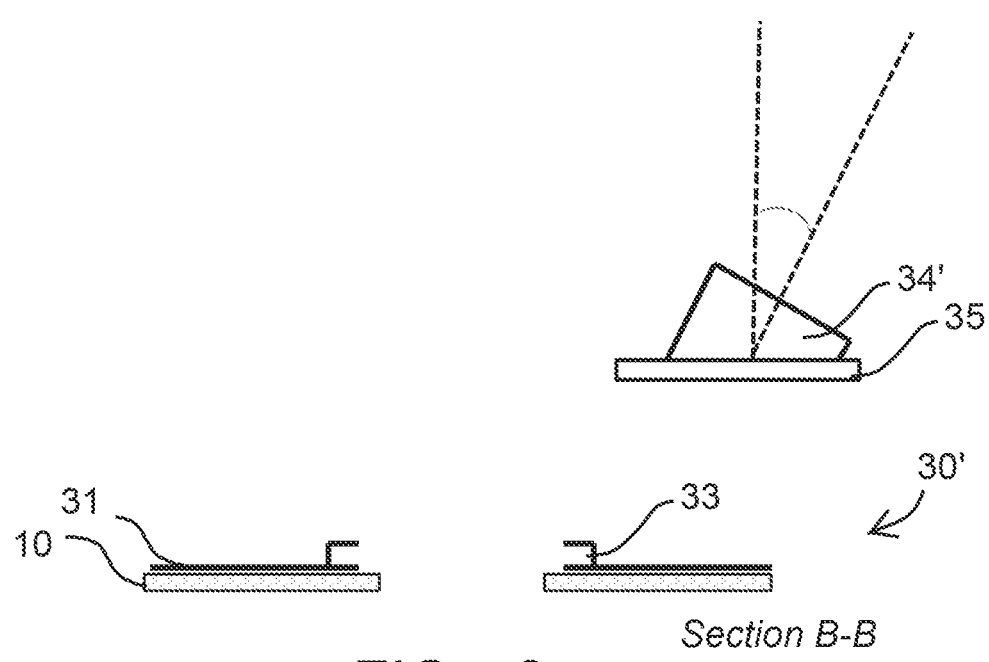
FIG. 9 shows a cross sectional view of an example aortic connector and an associated angle graft tube connector in accordance with some embodiments.

FIG. 8 shows another example aortic connector 30 having a direct coupling feature 33 to which the graft tube 18 or an angled tubular connector 34' can be attached. This approach still allows for an approach where the physician cuts the graft tube at a desired angle, but improves upon conventional approaches by providing a more stable interface for attaching the graft tube and maintains the diameter of the blood flow path entering the aorta. As shown, the aortic connector 30 includes a planar portion 31 formed of a flexible membrane and a suture ring 23. The coupling feature 33 surrounds the opening for providing blood flow into the aorta. The coupling feature 33 can be a cuff or any suitable coupling feature to allow for attachment of the tubular graft or an intervening connector, such as a separable angled tubular connector 34'. Such a connector is shown in FIG. 9 as a cross sectional view along section B-B of FIG. 8. The angled tubular graft portion 34' can include a bottom ring or flange that interfaces with the cuff so as to sealingly attach the angle graft portion 34' with the planar portion 31. The outflow graft 18 can then be attached to the connector by either directly attaching a distal portion of the outflow graft to the angled connector 34' or by use of an intervening connector. In some embodiments, the interfacing coupling between cuff 33 and ring 35 can include an alignment feature to fix the rotational orientation of the tubular connector within cuff 33 so as to control the direction at which the outflow graft extends.

Figure 10:
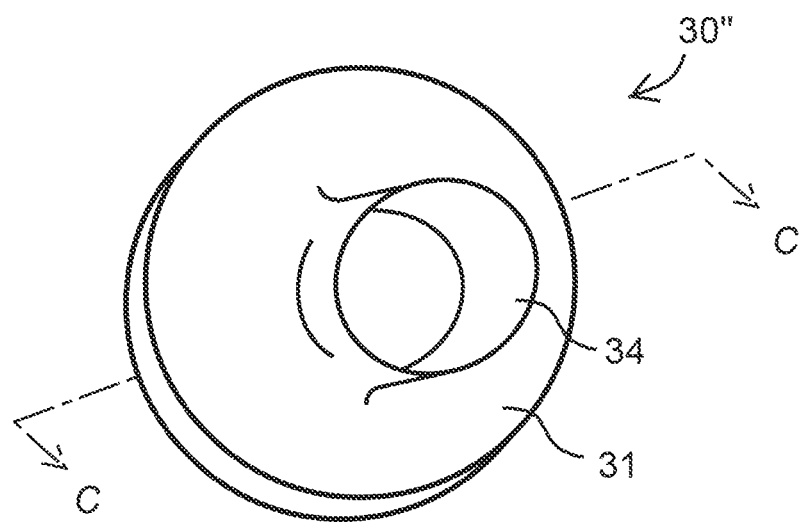
FIG. 10 shows a cross sectional view of an example aortic connector with a flange for implanting within the aorta in accordance with some embodiments.
Figure 11:
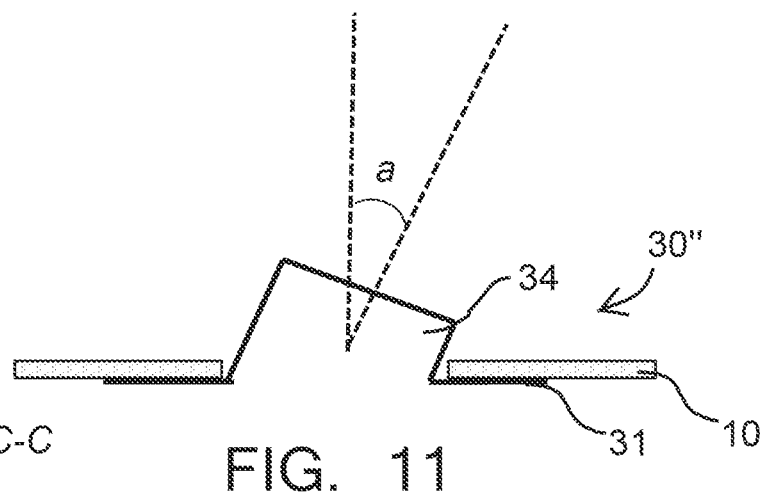
FIG. 11 shows a cross sectional view of an example aortic connector with a flange for implanting within the aorta in accordance with some embodiments.

FIG. 10 shows another embodiment of an aortic connector 30 in which the planar portion 31 from which the angled tubular connector 34 extends is configured to engage an inside surface of the wall of the aorta. As shown in the FIG. 11, which depicts a sectional view of the connector of FIG. 10 along section C-C after engagement with the inside surface of the aortic wall. In this embodiment, the planar portion 31 is defined as a flange and is substantially more rigid or semi-rigid as compared to the flexible membrane of the embodiments described above. The flange can include a suture ring to be connected to the wall of the aorta around the opening or can be formed of material to allow the flange to be directly sutured to the wall of the aorta. In some embodiments, the connector can include a capture ring above the flange that when tightened, engages the wall of the aorta around the opening. The flange can be formed of a porous or textured material, or can include a liner that is porous or textured, to facilitate tissue in-growth along the face of the flange engaged with the aortic wall. In some embodiments, the bottom surface of the flange that is exposed to blood flow through the aorta can be textured so as to promote formation of an intima layer to reduce likelihood of thrombus formation.

Figure 12A:
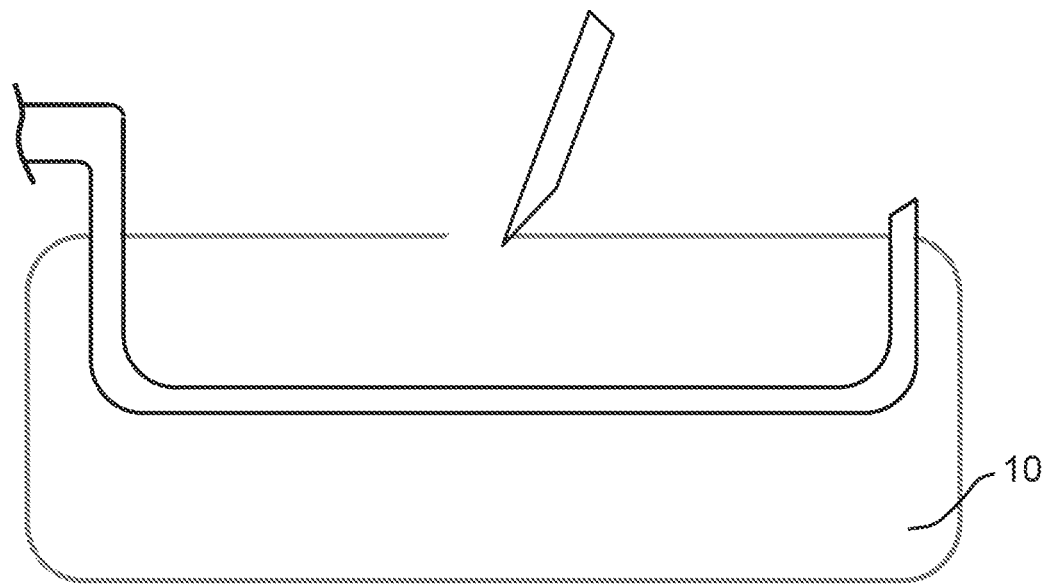
FIGS. 12A-12D show a method of attaching a graft tube of a blood pump to an aorta with an aortic connector in accordance with some embodiments.
Figure 12B:
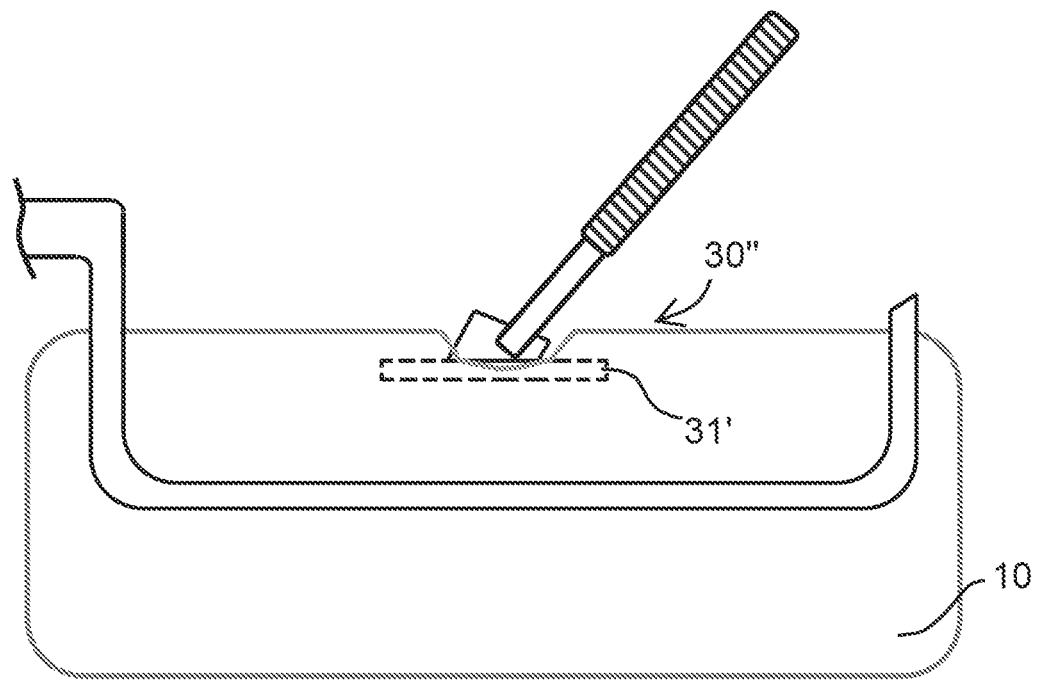
Figure 12C:
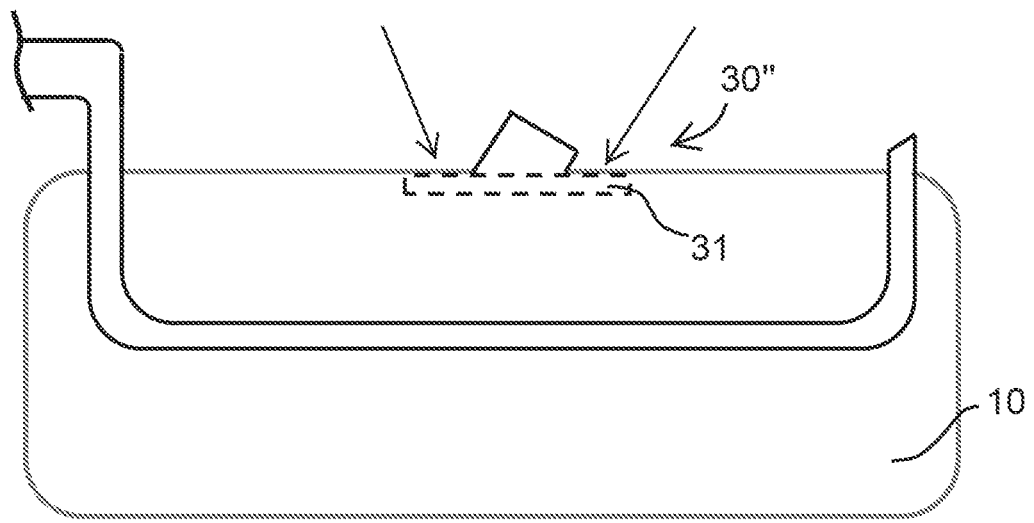
Figure 12D:
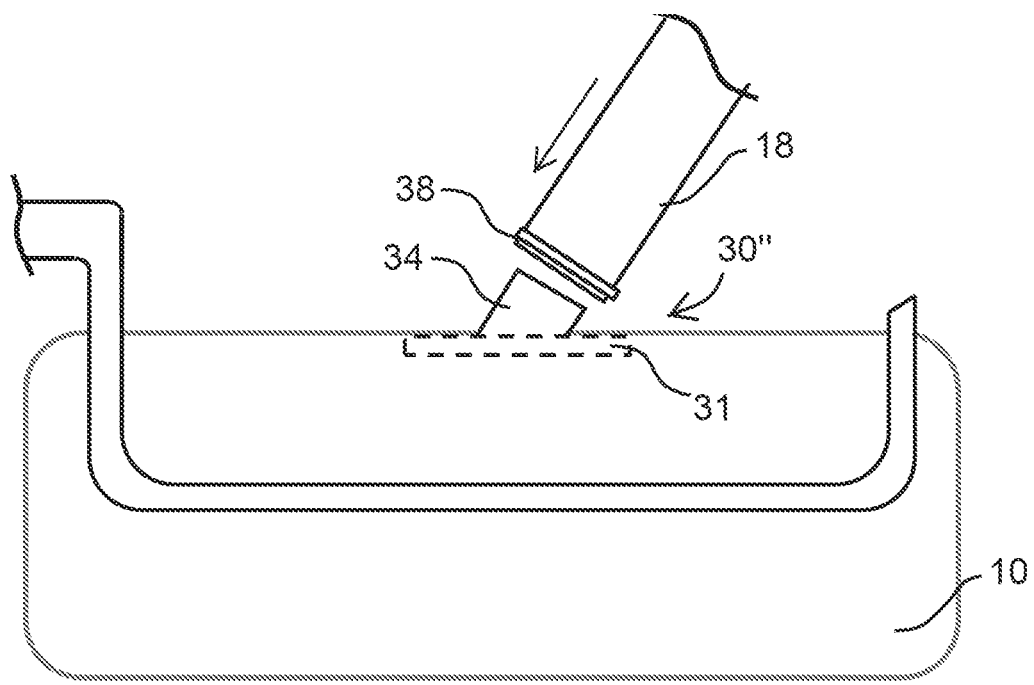

FIGS. 12A-12D illustrate a method of attaching an outflow graft tube to an aorta by use of an aortic connector 30 configured to be implanted on an inside surface of the aorta, for example the embodiment of FIG. 10. As shown in FIG. 12A, a side biting clamp is applied to create a hemostatic seal along a side portion of the aorta. A slit is made in the sealed portion of the aorta to form an opening for blood flow into the aorta. As show in FIG. 12B, the aortic connector 30' is inserted into the slit opening and pulled so as to engage a top surface of the planar portion 31 (e.g., flange) against the inside surface of the aorta and positioned so that the angled tubular connector 34 extends from the aorta in the desired direction. The flange can be secured to the wall around the opening, as indicated by the arrows in FIG. 12C. The flange can be secured by one or more sutures (e.g., a running suture), an adhesive, a capture ring, or any suitable means. As shown in FIG. 12D, the graft tube 18 can then be attached to the tubular connector 34 by an outflow tube connector 38, which can include any of a threaded connection, a snap-fit coupling, a capture ring, lock-and-twist coupling, a compression fitting, or any suitable coupling means.

Figure 13A:
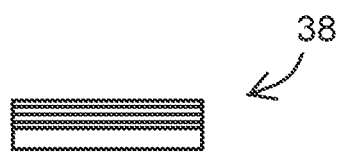
FIGS. 13A-13D show alternative coupling features suitable for use in coupling the aortic connector with a graft tube of a blood pump in accordance with some embodiments.
Figure 13B:
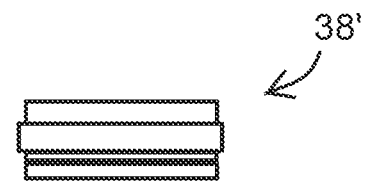
Figure 13C:
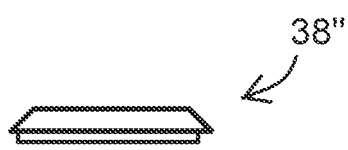
Figure 13D:
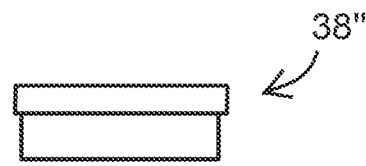
Figure 14:
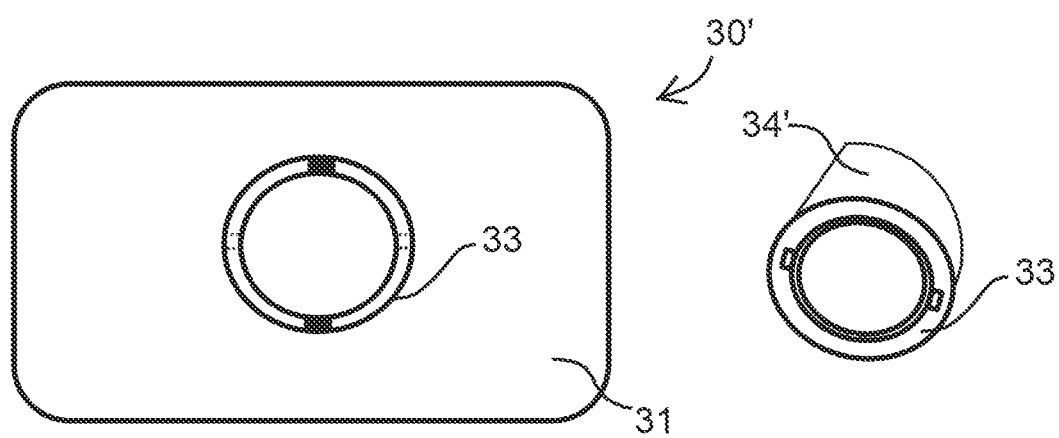
FIG. 14 shows an aortic connector having an alignment feature to facilitate alignment of an angled graft connector in accordance with some embodiments.

Various types of coupling features that can be used between the graft tube and aortic connector and/or between components of the aortic connector are shown in FIGS. 13A-13D. It is appreciated that any of the embodiments described herein could use any of these or similar type coupling features. FIG. 13A illustrates a threaded coupling, which can interface with a rotatable interfacing threaded ring or sleeve on a distal end of the graft tube or on an angled tubular connector. FIG. 13B illustrates a rotatable capture ring that can be used to capture a distal portion of the graft tube or tubular connector. FIG. 13C illustrates a barbed fitting over which a flexible distal portion of the graft tube can be fitted. Typically, such a fitting includes multiple barbs and the graft tube may be secured by tightening of an outer ring over the graft tube. FIG. 13D illustrates a cuff, which can be configured to fit with a corresponding component, such as in a snap-fit type coupling or a twist-and-lock type coupling. In some embodiments, the coupling features can include an alignment feature that fixes an orientation of the angled tubular connector in a particular orientation relative the planar portion. For example, FIG. 14 shows an aortic connector 31' having a separable angled tubular connector 34' with a twist-and-lock feature that allows the angled tubular connector to be secured and locked in fixed orientation when engaged and twisted. Semi-circular ramps sealingly engaging interfacing surfaces together when twisted and securing the angled tubular connector by receiving opposing tabs in one side of the connector within corresponding recesses in the other side of the connector. Such a configuration allows a physician to select an angled tubular connector from multiple interchangeable connectors having differing lengths, angles, or directional orientations, as desired for a particular application or patient anatomy.

Figure 15:
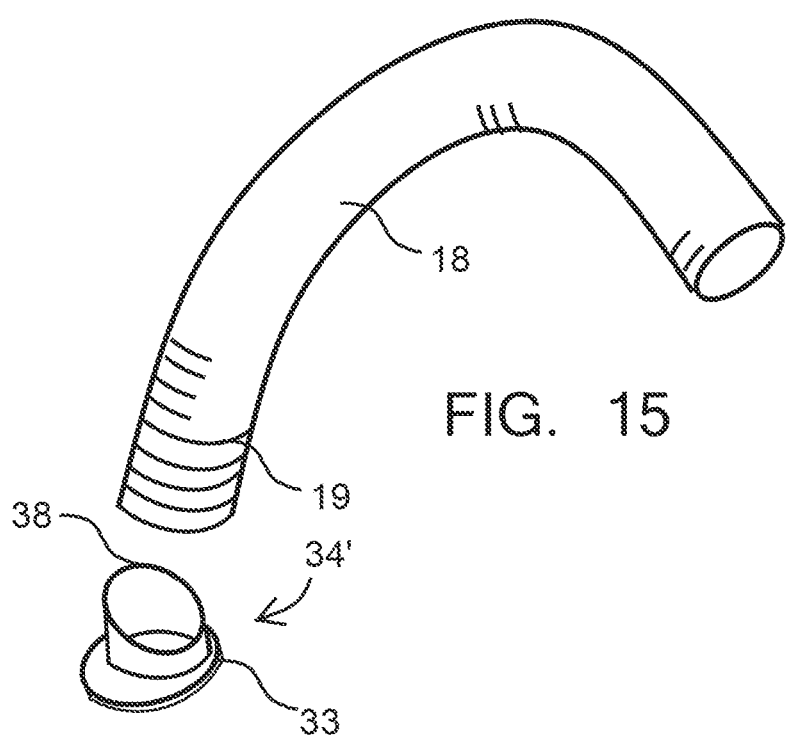
FIG. 15 shows an angled graft connector coupleable with a reinforcing ring of an outflow graft cut to a desired length in accordance with some embodiments.

FIG. 15 shows an angled tubular connector 34' of an aortic connector configured to couple with a distal portion of a graft tube 18 that has been cut to a desired length. In this embodiment, the graft tube 18 has a series of reinforcing hoops 19 along at least a distal portion thereof to resist crimping when flexed. Such reinforcing hoops can be discrete hoops or a spiral reinforcement along a length of the graft tube 18. The angled tubular connector 34 can include a coupling feature 38 that engages one of the reinforcing hoops 19. For example, a capture ring (not shown) can be included on aortic connector that receives and captures a reinforcing tube when the capture ring is tightened. Such a configuration allows the graft tube 18 to be cut to any desired length and sealingly coupled with the aortic connector.

Figure 16:
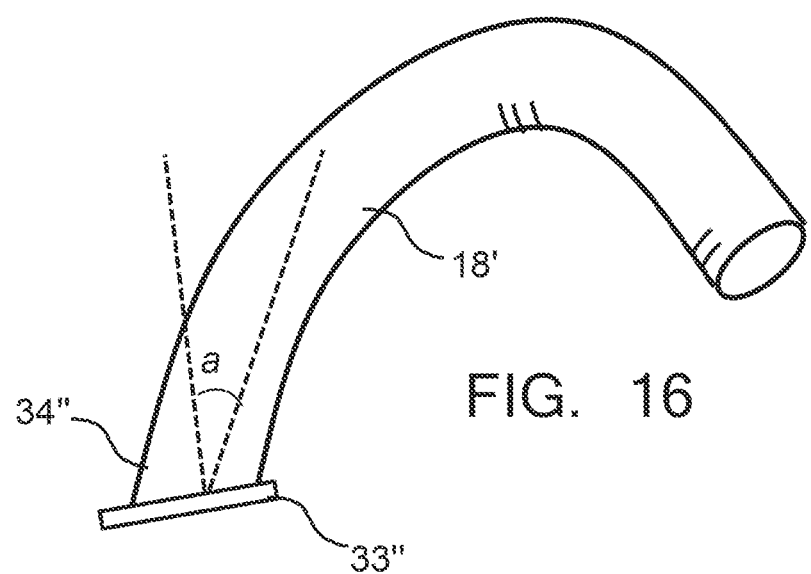
FIG. 16 shows an outflow graft having an integrated angled connector portion coupleable with an aortic connector in accordance with some embodiments.

FIG. 16 shows another embodiment having a graft tube 18' with an angled tubular connector 34" that is integrated into a distal portion thereof. Such an integrated tubular connector 34" can further include a distal coupling feature 33" that interfaces with a corresponding coupling feature in the aortic connector. Such a graft tube could be used with the aortic connector of FIG. 8 since the graft tube itself provides the set angle at which the graft tube meets the aorta. In such an embodiment, the graft tube could be cut to a desired length by cutting the opposite end of the graft tube where the graft tube joins the outlet of the blood pump.

Figure 17:
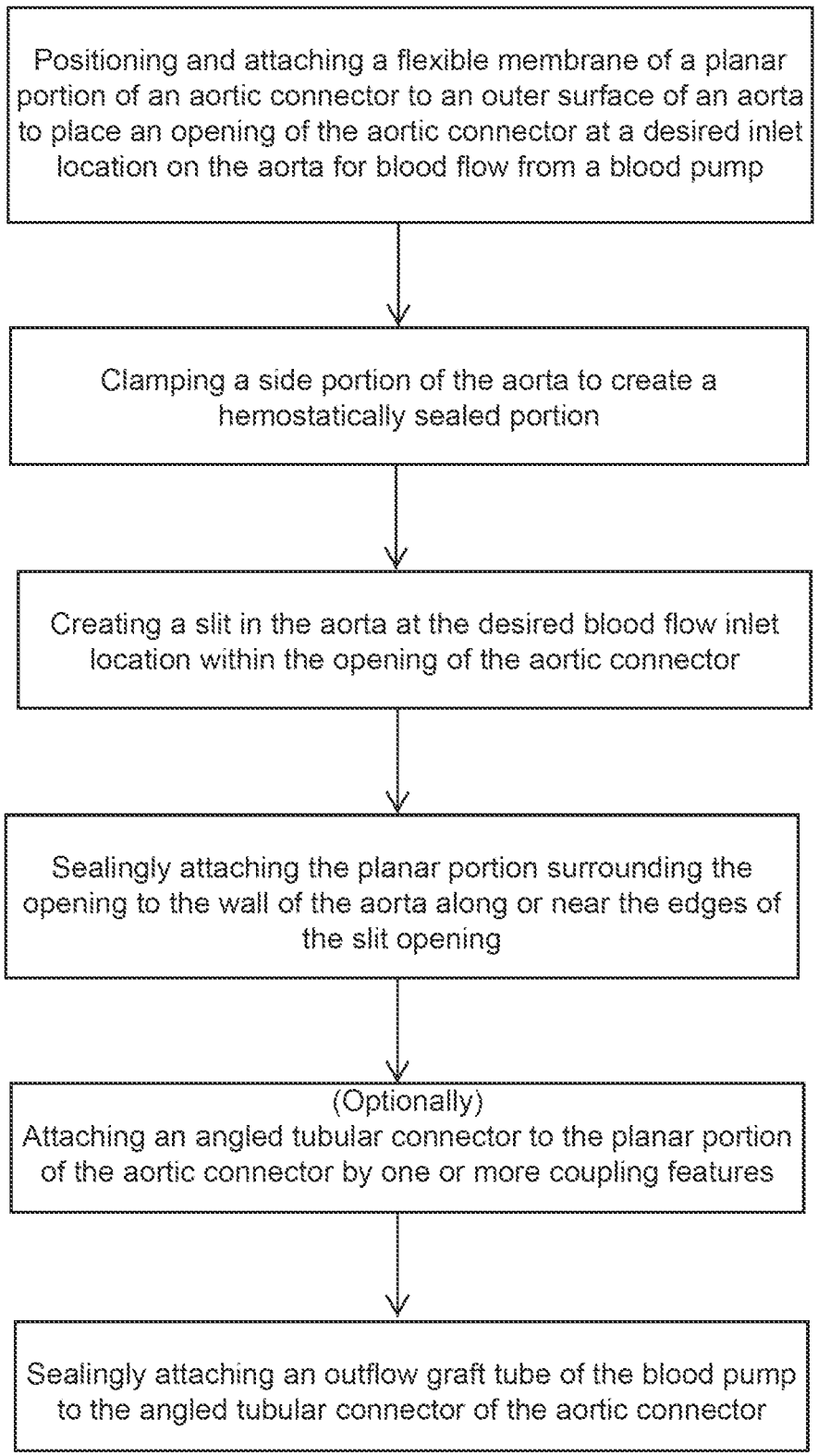
FIGS. 17-18 depict methods of attaching a graft tube of a blood pump to an aorta with an aortic connector in accordance with some embodiments.
Figure 18:
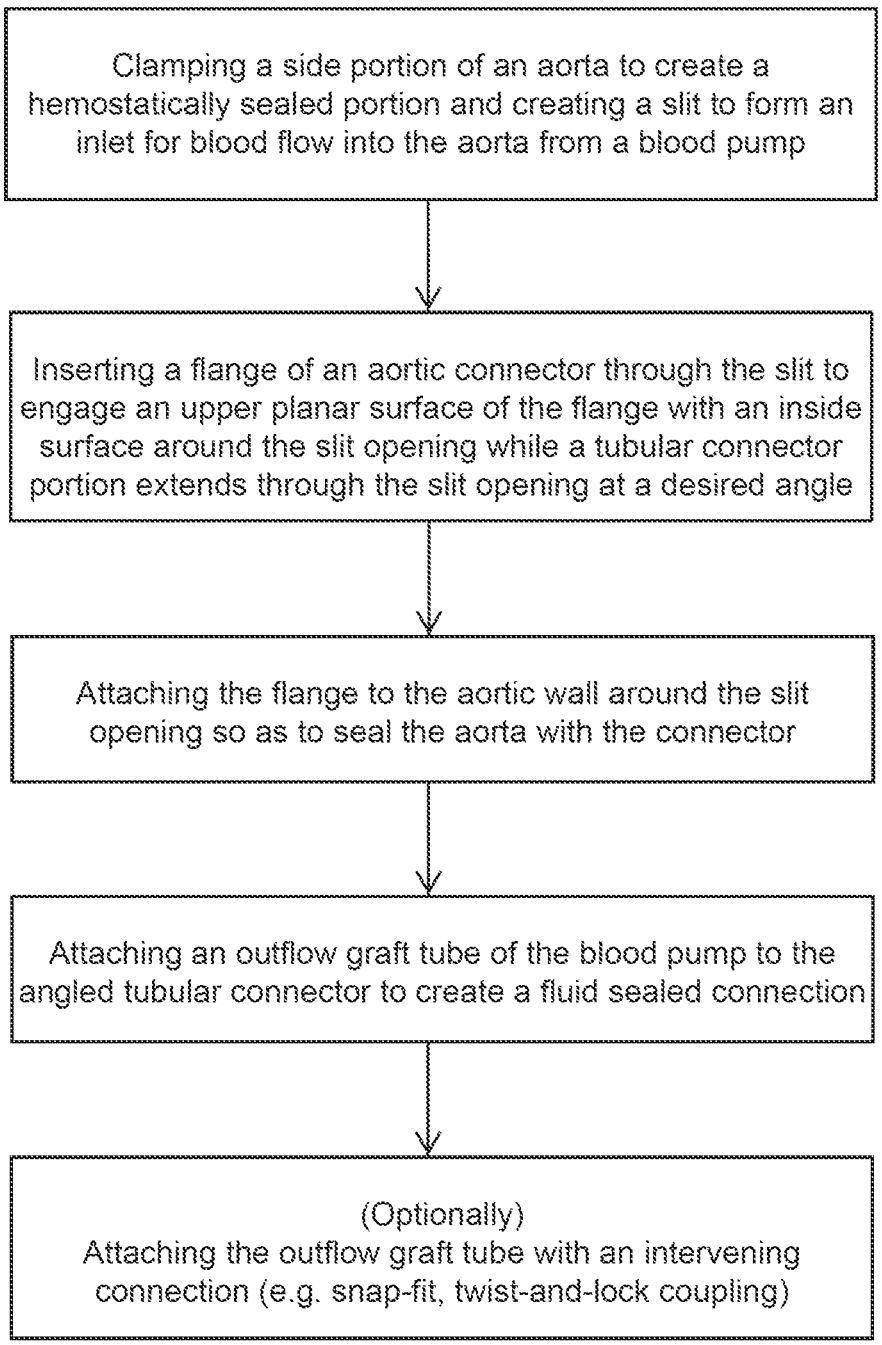

FIGS. 17 and 18 show methods of attaching an outflow graft tube of an implanted blood pump to the aorta with aortic connectors in accordance with some embodiments. It is appreciated that such methods can include use of direct suturing between components or can utilize any one or more of the coupling features described herein. It is further appreciated that such methods can include an initial step of selecting an aortic connector having a desired size and diameter of the inlet opening as well as a desired angle for blood flow into the aorta.

The method of FIG. 17 includes steps of: positioning and attaching a flexible membrane of a planar portion of an aortic connector to an outer surface of an aorta to place an opening of the aortic connector at a desired blood flow inlet location on the aorta for blood flow from a blood pump, and then, clamping a side portion of the aorta to create a hemostatically sealed portion. The method further includes creating a slit in the aorta at the desired blood flow inlet location within the opening of the aortic connector and sealingly attaching the planar portion surrounding the connector opening to aorta wall along or near the edges of the slit opening. Lastly, the method includes sealingly attaching an outflow graft tube of the blood pump to the angled tubular connector of the aortic connector. Such attachment can be formed by directly suturing the graft tube to the tubular connector, or can use one or more coupling features. Optionally, the angled tubular connector can be coupled to the planar portion of the aortic connector with a coupling feature, such as any of those described herein. In some embodiments, the angled tubular connector is integrated with the tubular connector. In various embodiments, intervening coupling features or fittings can be used to facilitate sealing connection between interfacing components.

The method of FIG. 18 includes steps of: clamping a side portion of an aorta to create a hemostatically sealed portion and creating a slit to form an inlet for blood flow into the aorta from a blood pump, and inserting a flange of an aortic connector through the slit. An upper planar surface of the flange is engaged with an inside surface around the slit opening while a tubular connector extends through the slit opening at a desired angle. The flange is attached to the aortic wall around the slit opening so as to seal the aorta with the connector. Lastly, the outflow graft tube of the blood pump is attached to the angled tubular connector to create a fluid sealed connection. Such attachment can include any of the coupling features described herein.

The foregoing presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim. The invention will be better understood upon reading the following description and examining the figures which accompany it.

All references, including publications, patent applications, and patents, cited herein are hereby incorporated by reference to the same extent as if each reference were individually and specifically indicated to be incorporated by reference and were set forth in its entirety herein.

What is claimed is:

1. A method of fluidly coupling a blood pump with an aorta of a patient, the method comprising:
   positioning a connector device comprising a tubular connector and an interface flange to interface the interface flange with the aorta, wherein the tubular connector has an inlet opening, an outlet opening, and a blood flow channel extending from the inlet opening to the outlet opening, wherein the interface flange extends from the outlet opening so as to provide a hemostatic seal between the aorta and the tubular connector when the interface flange is attached to the aorta, and wherein the tubular connector extends from the interface flange in a direction so that a flow of blood through the blood flow channel is discharged into the aorta at a desired angle through the outlet opening;
   securely attaching the interface flange to a wall of the aorta around the outlet opening of the tubular connector;
   incising a slit in the wall of the aorta to form an opening into the aorta; and
   fluidly coupling the inlet opening of the tubular connector with an outflow graft tube of the blood pump to facilitate blood flow from the blood pump into the aorta.

2. The method of claim 1, further comprising clamping a side portion of the aorta to create a hemostatic seal.

3. The method of claim 1, wherein securely attaching the interface flange to the wall of the aorta comprise suturing the interface flange along a suture ring extending around the outlet opening of the tubular connector.

4. The method of claim 1, wherein the interface flange comprises a flexible membrane such that positioning the connector device comprises interfacing the interface flange with an outside surface of the wall of the aorta.

5. The method of claim 4, further comprising securing an outer periphery of the flexible membrane to the outside surface of the wall of the aorta to promote tissue in-growth between the aorta and the flexible membrane.

6. The method of claim 1, wherein the interface flange is formed of a rigid or semi-rigid material such that positioning the connector device comprises inserting the interface flange through the opening into the aorta and engaging an inside surface of the wall of the aorta.

7. The method of claim 6, wherein securely attaching the interface flange to the wall of the aorta comprises suturing the interface flange to the wall of the aorta around the outlet opening of the tubular connector.

8. The method of claim 7, wherein securely attaching the interface flange to the wall of the aorta comprises engaging the wall of the aorta between the interface flange and an interfacing ring.

9. The method of claim 7, wherein fluidly coupling the inlet opening of the tubular connector to the outflow graft tube of the blood pump comprises securely attaching the tubular connector to the outflow graft tube by one or more intervening connectors.

10. The method of claim 7, wherein fluidly coupling the inlet opening of the tubular connector to the outflow graft tube of the blood pump comprises suturing the tubular connector to the outflow graft tube.

11. The method of claim 7, wherein fluidly coupling the inlet opening of the tubular connector to the outflow graft tube of the blood pump comprises engaging a distal portion of the outflow graft tube with a mechanical interface feature of the connector device.

12. The method of claim 1, further comprising:
    cutting the outflow graft tube to a desired length, the outflow graft tube having circumferential reinforcement ribs along at least a distal portion thereof,
    wherein fluidly coupling the inlet opening of the tubular connector to the outflow graft tube comprises capturing a reinforcement rib of the outflow graft tube with a mechanical interface feature of the tubular connector.

13. The method of claim 1, wherein interface flange and the tubular connector are separate components, the method further comprising:
    securely coupling the tubular connector to the interface flange by interfacing corresponding coupling features to form a fluid-tight seal between the interface flange and the tubular connector.

14. The method of claim 13, wherein securely coupling the tubular connector to the interface flange comprises engaging a flange of the tubular connector that extends outwardly along a distal portion of the tubular connector within a cuff extending around an opening of the interface flange.

15. The method of claim 1, further comprising positioning the tubular connector so as to extend from the aorta at a desired angle.

16. The method of claim 1, wherein the blood flow channel extends from the interface flange at an angle, the method further comprising:
    selecting the connector device or the tubular connector from a plurality of connector devices or tubular connectors defined with differing angles or diameters in accordance with a desired application or anatomy of the patient.

17. The method of claim 1, further comprising suturing edges of the wall of the aorta forming the opening into the aorta to an inner diameter of the tubular connector.

18. The method of claim 1, wherein the slit is incised in the wall of the aorta after securely attaching the interface flange to the wall of the aorta via access through the blood flow channel of the tubular connector.

* * * * *